United States Patent
Shinde et al.

(10) Patent No.: US 12,365,657 B2
(45) Date of Patent: Jul. 22, 2025

(54) PREPARATION OF 2-CHLORO-1-(2-CHLOROTHIAZOL-5-YL) ETHANONE

(71) Applicant: BASF SE, Ludwigshafen (DE)

(72) Inventors: Harish Shinde, Navi Mumbai (IN); Rahul Kaduskar, Navi Mumbai (IN); Christopher Koradin, Ludwigshafen (DE); Martin John McLaughlin, Ludwigshafen (DE); Roland Goetz, Ludwigshafen (DE); Sunil Khamkar, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 443 days.

(21) Appl. No.: 17/641,989

(22) PCT Filed: Sep. 28, 2020

(86) PCT No.: PCT/EP2020/077090
§ 371 (c)(1),
(2) Date: Mar. 10, 2022

(87) PCT Pub. No.: WO2021/063880
PCT Pub. Date: Apr. 8, 2021

(65) Prior Publication Data
US 2024/0051929 A1    Feb. 15, 2024

(30) Foreign Application Priority Data

Oct. 4, 2019   (EP) .................................. 19201400
Oct. 23, 2019  (EP) .................................. 19204737

(51) Int. Cl.
*C07D 277/32*    (2006.01)

(52) U.S. Cl.
CPC .................................. *C07D 277/32* (2013.01)

(58) Field of Classification Search
CPC .................................................... C07D 277/32
See application file for complete search history.

(56) References Cited

FOREIGN PATENT DOCUMENTS

| WO | WO-02/02654 A1 | 1/2002 |
| WO | WO-2014/164084 A2 | 10/2014 |
| WO | WO-2017/021549 A1 | 2/2017 |
| WO | WO-2018/177970 A1 | 10/2018 |
| WO | WO-2018/197541 A1 | 11/2018 |

OTHER PUBLICATIONS

European Search Report for EP Patent Application No. 19204737.1, Issued on Feb. 7, 2020, 3 pages.
Chalopin et al., Second generation of thiazolylmannosides, FimH antagonists for *E. coli*-induced Crohn's disease, Org. Biomol. Chem., 14(16):3913-25 (2016).
International Application No. PCT/EP2020/077090, International Search Report and Written Opinion, mailed Jan. 22, 2021.

*Primary Examiner* — Shawquia Jackson
(74) *Attorney, Agent, or Firm* — MARSHALL, GERSTEIN & BORUN LLP

(57) ABSTRACT

The present invention relates to a process for the preparation 2-chloro-1-(2-chlorothiazol-5-yl)ethanone.

13 Claims, No Drawings

PREPARATION OF 2-CHLORO-1-(2-CHLOROTHIAZOL-5-YL) ETHANONE

CROSS-REFERENCE TO RELATED APPLICATIONS

This is the U.S. national phase of International Application No. PCT/EP2020/077090, filed Sep. 28, 2020, which claims the benefit of European Patent Application No. 19201400.9, filed on Oct. 4, 2019, and European Patent Application No. 19204737.1, filed Oct. 23, 2019.

FIELD OF THE INVENTION

The present invention relates to a process for the preparation 2-chloro-1-(2-chlorothiazol-5-yl)ethanone.

BACKGROUND OF THE INVENTION

2-Chloro-1-(2-chlorothiazol-5-yl)ethanone is a valuable intermediate in the synthesis of pyridinium compounds that are inter alia known from WO 2014/164084 A1. These compounds show excellent insecticidal properties.

WO 2018/197541 A1 and WO/202654 A1 disclose a synthetic route to these pyridinium compounds which includes the reaction of chloro-(2-chlorthiazol-5-yl)magnesium species and 2-chloro-N-methoxy-N-methyl-acetamide to form 2-chloro-1-(2-chlorothiazol-5-yl)ethanone.

T. Chalopin et al., Second generation of thiazolylmannosides, FimH antagonists for *E. coli*-induced Crohn's disease, Org. Biomol. Chem., 2016, 14, 3913-3925, describes the synthesis of 1-(2-chlorothiazol-5-yl)ethanone from thiourea.

However, the processes of the prior art suffer from several drawbacks, such as high effluent load and metal salt load, low yields, low selectivity and the use of toxic solvents.

Hence, it is an object of the presently claimed invention to provide an economical process for the preparation of 2-chloro-1-(2-chlorothiazol-5-yl)ethanone that provides 2-chloro-1-(2-chlorothiazol-5-yl)ethanone in a high overall yield, i.e. 85% or ≥80%, with high selectivity, that can be easily controlled.

SUMMARY OF THE INVENTION

Surprisingly, it has been found that the controlled cyclization of 1,3-bis(dimethylaminomethyl-ene)thiourea and chloroacetone by adding chloroacetone at a specific addition rate, followed by acidic treatment, Sandmeyer reaction and chlorination leads to the formation of 2-chloro-1-(2-chlorothiazol-5-yl)ethanone in high yield with high selectivity within a reasonable process time.

Accordingly, in one aspect, the presently claimed invention is directed to a process for the preparation of 2-chloro-1-(2-chlorothiazol-5-yl)ethanone comprising at least the steps of:
 a) cyclization of 1,3-bis(dimethylaminomethylene)thiourea and chloroacetone to form N'-(5-acetylthiazol-2-yl)-N,N-dimethyl-formamidine,
 b) subjecting (5-acetylthiazol-2-yl)-N,N-dimethyl-formamidine to at least one acid to form 1-(2-aminothiazol-5-yl)ethanone,
 c) Sandmeyer reaction of 1-(2-aminothiazol-5-yl)ethanone to form 1-(2-chlorothiazol-5-yl)ethanone, and
 d) chlorination of 1-(2-chlorothiazol-5-yl)ethanone to form 2-chloro-1-(2-chlorothiazol-5-yl)ethanone, wherein in step a) chloroacetone is added at a rate in the range of ≥2.0 vol.-%/minute to ≤8.0 vol.-%/minute, based on the total volume of chloroacetone.

DETAILED DESCRIPTION

Before the present compositions and formulations of the presently claimed invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms 'first', 'second', 'third' or 'a', 'b', 'c', etc. and the like in the description and in the claims, are used for distinguishing between similar elements and not necessarily for describing a sequential or chronological order. It is to be understood that the terms so used are inter-changeable under appropriate circumstances and that the embodiments of the presently claimed invention described herein are capable of operation in other sequences than described or illustrated herein. In case the terms 'first', 'second', 'third' or '(A)', '(B)' and '(C)' or '(a)', '(b)', '(c)', '(d)', 'i', 'ii' etc. relate to steps of a method or use or assay there is no time or time interval coherence between the steps, that is, the steps may be carried out simultaneously or there may be time intervals of seconds, min, hours, days, weeks, months or even years between such steps, unless otherwise indicated in the application as set forth herein above or below.

Furthermore, the ranges defined throughout the specification include the end values as well, i.e. a range of ≥1 to 10 implies that both 1 and 10 are included in the range. For the avoidance of doubt, applicant shall be entitled to any equivalents according to applicable law.

In the following passages, different aspects of the presently claimed invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to 'one embodiment' or 'an embodiment' means that a particular feature, structure or characteristic described in connection with the embodiment is included in at least one embodiment of the presently claimed invention. Thus, appearances of the phrases 'in one embodiment' or 'in an embodiment' in various places throughout this specification are not necessarily all referring to the same embodiment but may refer to the same embodiment. Further, as used in the following, the terms "preferably", "more preferably", "even more preferably", "most preferably" and "in particular" or similar terms are used in conjunction with optional features, without restricting alternative possibilities. Thus, features introduced by these terms are optional features and are not intended to restrict the scope of the claims in any way.

Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the presently claimed invention, and form different embodiments, as would be understood by those in the art. For example, in the appended claims, any of the claimed embodiments can be used in any combination.

Further, it shall be noted that the terms "at least one", "one or more" or similar expressions indi-cating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Condensation

The process of the presently claimed invention uses 1,3-bis(dimethylaminomethylene)thiourea as a starting material.

In a preferred embodiment, 1,3-bis(dimethylaminomethylene)thiourea is obtained by condensation of thiourea with dimethylformamide di-alkyl acetal, more preferably dimethylformamide dimethyl acetal.

In a preferred embodiment, the condensation is carried out a temperature in the range of ≥40° C. to ≤70° C. and more preferably a temperature in the range of ≥50° C. to ≤65° C.

In a preferred embodiment, the condensation is carried out in at least one solvent selected from the group consisting of monochlorobenzene, o-dichloro-benzene, nitrobenzene, dichloromethane, dichloroethane, chloroform, toluene, o-xylene, m-xylene and p-xylene.

Step a: Cyclization

In step a) of the process according to the presently claimed invention 1,3-bis(dimethylaminomethylene)thiourea and chloroacetone react to form N'-(5-acetylthiazol-2-yl)-N,N-dimethyl-formamidine, whereby chloroacetone is added to a suspension of 1,3-bis(dimethylaminomethylene)thiourea at a rate in the range of ≥2.0 vol.-%/minute to ≤8.0 vol.-%/minute, based on the total volume of chloroacetone.

In a preferred embodiment, chloroacetone is added at a rate in the range of ≥2.0 vol.-%/minute to ≤7.0 vol.-%/minute, more preferably at a rate in the range of ≥2.0 vol.-%/minute to ≤6.0 vol.-%/minute, even more preferably at a rate in the range of ≥3.0 vol.-%/minute to ≤6.0 vol.-%/minute, based on the total volume of chloroacetone. e.g. an addition of a total volume of 650 mL chloroacetone within 20 minutes is equivalent to an addition of 32.5 mL per minute which translates into an addition rate of 5.0 vol.-%/minute, based on the total volume of chloroacetone.

The specific addition rate allows for, on the one hand, conducting the reaction in a controlled manner at a fast addition of chloroacetone, i.e. any harsh increase in the temperature of the reaction mixture is prevented, and, on the other hand, reducing the amount of impurities at a slow addition of chloroacetone.

In a preferred embodiment, chloroacetone is added as a solution in at least one solvent selected from the group consisting of monochlorobenzene, o-dichloro-benzene, nitrobenzene, dichloromethane, dichloroethane, chloroform, toluene, o-xylene, m-xylene and p-xylene; more preferably at least one solvent selected from the group consisting of monochlorobenzene, o-dichloro-benzene, nitrobenzene, o-xylene, m-xylene and p-xylene; most preferably the at least one solvent is monochlorobenzene.

In a preferred embodiment, step a) is carried out at a temperature the range of ≥40° C. to ≤75° C., more preferably at a temperature in the range of ≥40° C. to ≤70° C.

In a preferred embodiment, step a) is carried out in at least one solvent selected from the group consisting of monochlorobenzene, o-dichloro-benzene, nitrobenzene, dichloromethane, dichloroethane, chloroform, toluene, o-xylene, m-xylene and p-xylene; more preferably at least one solvent selected from the group consisting of monochlorobenzene, o-dichloro-benzene, nitrobenzene, o-xylene, m-xylene and p-xylene; most preferably the at least one solvent is monochlorobenzene.

In a preferred embodiment, in step a) the concentration of chloroacetone in the at least one solvent is in the range of ≥100 g/L to ≤800 g/L, more preferably in the range of ≥200 g/L to ≤700 g/L, most preferably in the range of ≥400 g/L to ≤600 g/L.

In a preferred embodiment, in step a) the concentration of 1,3-bis(dimethylaminomethylene)-thiourea in the at least one solvent is in the range of ≥54 g/L to ≤220 g/L.

In a preferred embodiment, in step a) the molar ratio of chloroacetone to 1,3-bis(dimethylaminomethylene)thiourea is in the range of ≥1.20:1.00 to ≤1.01:1.00, more preferably in the range of ≥1.10:1.00 to ≤1.01:1.00.

In another preferred embodiment, step a) is carried out in the absence of any amine, more preferably step a) is carried out in the absence of any tertiary amine and secondary amine, even more preferably in the absence of any amine selected from the group consisting of trimethyla-mine, triethylamine, methyldiethylamine, tripropylamine, triisopropylamine, diisopropylethyla-mine, diisopropylamine and dibutylamine.

Step b: Hydrolysis

In step b) of the process according to the presently claimed invention, N'-(5-acetylthiazol-2-yl)-N,N-dimethylformamidine is subjected to at least one acid to form 1-(2-aminothiazol-5-yl)ethanone.

In a preferred embodiment, in step b) at least one acid is selected from inorganic acids and organic acids. Preferably, the inorganic acids are selected from the group consisting of sulfuric acid, hydrochloric acid, phosphoric acid, perchloric acid, nitric acid, nitrous acid, *sulphurous* acid, chloric acid, chlorous acid, boric acid and hypochlorous acid. Preferably, the organic acids are selected from the group consisting of lactic acid, acetic acid, formic acid, citric acid, oxalic acid, uric acid, malic acid, methane sulfonic acid, trifluoromethane sulfonic acid, trichloromethane sulfonic acid, and p-toluene sulfonic acid. In a more preferred embodiment, in step b) the at least one acid is hydrochloric acid or sulfuric acid.

In a preferred embodiment, in step b) the pH is in the range of ≥−1.5 to ≤8.0.

In a preferred embodiment, step b) is carried out in at least one solvent selected from the group consisting of monochlorobenzene, o-dichloro-benzene, nitrobenzene, dichloromethane, dichloroethane, chloroform, toluene, o-xylene, m-xylene and p-xylene; more preferably at least one solvent selected from the group consisting of monochlorobenzene, o-dichloro-benzene, nitrobenzene, o-xylene, m-xylene and p-xylene; most preferably the at least one solvent is monochlorobenzene.

In a preferred embodiment, step b) is carried out at a temperature the range of ≥20° C. to ≤110° C., more preferably at a temperature the range of ≥40° C. to ≤90° C., even more preferably at a temperature the range of ≥50° C. to ≤70° C.

Step c: Sandmeyer Reaction

In step c) of the process according to the presently claimed invention, 1-(2-aminothiazol-5-yl)ethanone is converted to 1-(2-chlorothiazol-5-yl)ethanone via a Sandmeyer reaction.

In a preferred embodiment, step c) is carried out in the presence of at least one nitrosating agent, preferably selected from the group consisting of sodium nitrite, potassium nitrite and alkyl nitrites, and at least one chlorine source, preferably selected from the group consisting of cop-per(II) chloride, tetraalkylammonium chloride, sodium chloride, and hydrochloric acid. In a more preferred embodiment, the at least one nitrosating agent is sodium nitrite and the at least one chlorine source is sodium chloride and/or hydrochloric acid. In a preferred embodiment, the molar ratio of the at least one chlorine source to 1-(2-aminothiazol-5-yl)ethanone is in the range of 2.0:1.0 to ≤1.0:1.0.

In a preferred embodiment, step c) is carried out in the presence of at least one catalyst, more preferably the at least one catalyst is selected from the group consisting of copper, cop-per(I)halogenides, copper(II)sulfate and copper(II)halogenides, even more preferably the at least one catalyst is copper(II)sulfate.

In a preferred embodiment, in step c) the molar ratio of the at least one catalyst to 1-(2-aminothiazol-5-yl)ethanone is in the range of ≥0.01:1.0 to ≤0.05:1.0.

In another preferred embodiment, step c) is carried out at a temperature in the range of ≥−10° C. to ≤40° C., more preferably at a temperature in the range of ≥−10° C. to ≤20° C.

In a preferred embodiment, step c) is carried out in at least one solvent selected from the group consisting of monochlorobenzene, o-dichloro-benzene, nitrobenzene, dichloromethane, dichloroethane, chloroform, toluene, o-xylene, m-xylene and p-xylene; more preferably at least one solvent selected from the group consisting of monochlorobenzene, o-dichloro-benzene, nitrobenzene, o-xylene, m-xylene and p-xylene; most preferably the at least one solvent is monochlorobenzene.

In a preferred embodiment, the steps a), b) and c) are carried out in a one-pot reaction, more preferably the steps a), b) and c) are carried out in a one-pot reaction in which monochlorobenzene is used as a solvent.

Step d: Chlorination

In step d) of the process according to the presently claimed invention, 1-(2-chlorothiazol-5-yl)ethanone is converted to 2-chloro-1-(2-chlorothiazol-5-yl)ethanone via selective chlorination.

In a preferred embodiment, step d) is carried out in at least one polar solvent selected from the group consisting of sulfoxides, sulfolane, acetonitrile, dichloromethane, dichloroethane, monochlorobenzene, o-dichlorobenzene, toluene, dimethylcarbonate, ethylenecarbonate, water, acetic acid, formic acid, tetrahydrofuran, 2-methyl-tetrahydrofuran, dimethylformamide, dimethyla-cetamide, methanol, ethanol, isopropanol, tert-butanol, n-butanol, tert-amyl alcohol, and ionic liquids, more preferably the at least one solvent is acetonitrile. Suitable ionic liquids are selected from the group consisting of 1-alkyl-3-methyl imidazolium tetrafluoroborate, 1-alkyl-3-methyl imidazolium halides, N-alkyl pyridiniums tetrafluoroborate and pentafluorophosphate deriva-tives.

In a preferred embodiment, step d) is carried out in the presence of at least one chlorinating agent, more preferably the at least one chlorinating agent is selected from the group consisting of chlorine gas, cyanuric chloride, 1,3-dichloro-5,5-dimethylhydantoin, N-chlorosuccinimide, N-chlorophthalimide, sodium dichloroisocyanurate, trimethylsilyl chloride, oxalyl chloride, methanesulfonyl chloride, sulfuryl chloride, acetyl chloride, triethylammonium trichloride, alkylimidazolium chloride, sodium chloride and $FeCl_3$.

In a preferred embodiment, step d) is carried out in the presence of at least one acid catalyst which is selected from inorganic acids and organic acids can be used. Suitable inorganic acids include sulfuric acid, hydrochloric acid, phosphoric acid, perchloric acid, nitric acid, nitrous acid, *sulphurous* acid, chloric acid, chlorous acid, boric acid and hypochlorous acid. Suitable organic acids include lactic acid, acetic acid, formic acid, citric acid, oxalic acid, uric acid, malic acid, methane sulfonic acid, trifluoromethane sulfonic acid, trichloromethane sulfonic acid, and p-toluene sulfonic acid.

In a preferred embodiment, step d) is carried out at a temperature the range of ≥0° C. to ≤40° C., more preferably at a temperature in the range of ≥0° C. to ≤20° C.

Advantages

The presently claimed invention is associated with at least one of the following advantages:

(i) The reaction sequence from 1,3-bis(dimethylaminomethylene)thiourea to 1-(2-chlorothiazol-5-yl)ethanone can be carried out in one pot.

(ii) 1-(2-Chlorothiazol-5-yl)ethanone is provided in a high overall yield and with a high purity from 1,3-bis(dimethylaminomethylene)thiourea.

(iii) 2-Chloro-1-(2-chlorothiazol-5-yl)ethanone is provided in a high overall yield with high selectivity from 1,3-bis(dimethylaminomethylene)thiourea.

(iv) The process of the presently claimed invention uses process benign solvents.

(v) The process of the presently claimed invention involves a low effluent load and a low metal load.

(vi) The process of the presently claimed invention is safe and can be easily controlled.

(vii) The process of the presently claimed invention is economical, because chloroacetone is added within a reasonable process time.

In the following, there is provided a list of embodiments to further illustrate the present disclosure without intending to limit the disclosure to the specific embodiments listed below.

EMBODIMENTS

1. A process for the preparation of 2-chloro-1-(2-chlorothiazol-5-yl)ethanone comprising at least the steps of:
   a) cyclization of 1,3-bis(dimethylaminomethylene) thiourea and chloroacetone to form N'-(5-acetylthiazol-2-yl)-N,N-dimethyl-formamidine,
   b) subjecting (5-acetylthiazol-2-yl)-N,N-dimethyl-formamidine to at least one acid to form 1-(2-aminothiazol-5-yl)ethanone,
   c) Sandmeyer reaction of 1-(2-aminothiazol-5-yl)ethanone to form 1-(2-chlorothiazol-5-yl)ethanone, and
   d) chlorination of 1-(2-chlorothiazol-5-yl)ethanone to form 2-chloro-1-(2-chlorothiazol-5-yl)ethanone,
   wherein in step a) chloroacetone is added at a rate in the range of ≥2.0 vol.-%/minute to ≤8.0 vol.-%/minute, based on the total volume of chloroacetone.

2. The process according to embodiment 1, wherein in step a) chloroacetone is added at a rate in the range of ≥2.0 vol.-%/minute to ≤7.0 vol.-%/minute, based on the total volume of chloroacetone.

3. The process according to embodiment 1, wherein 1,3-bis(dimethylaminomethylene)thiourea is obtained by condensation of thiourea with dimethylformamide dialkyl acetal.
4. The process according to embodiment 3, wherein the condensation is carried out at temperature in the range of ≥40° C. to ≤70° C.
5. The process according to embodiment 3 or 4, wherein the condensation is carried out in at least one solvent selected from the group consisting of monochlorobenzene, o-dichloro-benzene, nitrobenzene, dichloromethane, dichloroethane, chloroform, toluene, o-xylene, m-xylene and p-xylene.
6. The process according to any of embodiments 1 to 5, wherein step a) is carried out at a temperature the range of ≥40° C. to ≤75° C.
7. The process according to any of embodiments 1 to 6, wherein step a) is carried out in at least one solvent selected from the group consisting of monochlorobenzene, o-dichloro-benzene, nitrobenzene, dichloromethane, dichloroethane, chloroform, toluene, o-xylene, m-xylene and p-xylene.
8. The process according to embodiment 7, wherein in step a) the concentration of chloroacetone in the at least one solvent is in the range of ≥100 g/L to ≤800 g/L.
9. The process according to any of embodiments 1 to 8, wherein in step a) the concentration of 1,3-bis(dimethylaminomethylene)thiourea in the at least one solvent is in the range of ≥54 g/L to ≤220 g/L.
10. The process according to any of embodiments 1 to 9, wherein in step a) the molar ratio of chloroacetone to 1,3-bis(dimethylaminomethylene)thiourea is in the range of ≥1.20:1.00 to ≤1.01:1.00.
11. The process according to any of embodiments 1 to 10, wherein step a) is carried out in the absence of any amine.
12. The process according to any of embodiments 1 to 11, wherein in step b) the at least one acid is selected from inorganic acids and organic acids.
13. The process according to embodiment 12, wherein the inorganic acids are selected from the group consisting of sulfuric acid, hydrochloric acid, phosphoric acid, perchloric acid, nitric acid, nitrous acid, *sulphurous* acid, chloric acid, chlorous acid, boric acid and hypochlorous acid.
14. The process according to embodiment 12, wherein the organic acids are selected from the group consisting of lactic acid, acetic acid, formic acid, citric acid, oxalic acid, uric acid, malic acid, methane sulfonic acid, trifluoromethane sulfonic acid, trichloromethane sulfonic acid, and p-toluene sulfonic acid.
15. The process according to embodiment 12, wherein the at least one acid is hydrochloric acid or sulfuric acid.
16. The process according to any of embodiments 1 to 15, wherein in step b) the pH is in the range of ≥−1.5 to ≤8.0.
17. The process according to any of embodiments 1 to 16, wherein step b) is carried out in at least one solvent selected from the group consisting of monochlorobenzene, o-dichloro-benzene, nitrobenzene, dichloromethane, dichloroethane, chloroform, toluene, o-xylene, m-xylene and p-xylene.
18. The process according to any of embodiments 1 to 17, wherein step b) is carried out at a temperature the range of ≥20° C. to ≤110° C.
19. The process according to any of embodiments 1 to 18, wherein step c) is carried out in the presence of at least one nitrosating agent and at least one chlorine source.
20. The process according to embodiment 19, wherein the at least one nitrosating agent is selected from the group consisting of sodium nitrite, potassium nitrite and alkyl nitrites.
21. The process according to embodiment 19, wherein the at least one chlorine source is selected from the group consisting of copper(II)chloride, tetraalkylammonium chloride, sodium chloride, and hydrochloric acid.
22. The process according to any of embodiments 19 to 21, wherein the molar ratio of the at least one chlorine source to 1-(2-aminothiazol-5-yl)ethanone is in the range of ≥2.0:1.0 to ≤1.0:1.0.
23. The process according to any of embodiments 1 to 22, wherein step c) is carried out in the presence of at least one catalyst.
24. The process according to embodiment 23, wherein the at least one catalyst is selected from the group consisting of copper, copper(I)halogenides, copper(II)sulfate and cop-per(II)halogenides.
25. The process according to embodiment 23 or 24, wherein in step c) the molar ratio of the at least one catalyst to 1-(2-aminothiazol-5-yl)ethanone is in the range of ≥0.01:1.0 to ≤0.05:1.0.
26. The process according to any of embodiments 1 to 25, wherein step c) is carried out at a temperature in the range of ≥−10° C. to ≤40° C.
29. The process according to any of embodiments 1 to 26, wherein step d) is carried out in at least one polar solvent selected from the group consisting of sulfoxides, sulfolane, acetonitrile, dichloromethane, dichloroethane, monochlorobenzene, o-dichlorobenzene, dimethyl carbonate, ethylene carbonate and ionic liquids.
28. The process according to any of embodiments 1 to 27, wherein step d) is carried out in the presence of at least one chlorinating agent.
29. The process according to embodiment 28, wherein the at least one chlorinating agent is selected from the group consisting of chlorine, cyanuric chloride, 1,3-dichloro-5,5-dimethylhydantoin, N-chlorosuccinimide, N-chlorophthalimide, sodium dichloroisocyanurate, trimethylsilyl chloride, oxalyl chloride, methanesulfonyl chloride and sulfuryl chloride, acetyl chloride, triethylammonium trichloride, alkylimidazolium chloride, sodium chloride and $FeCl_3$.
30. The process according to any of embodiments 1 to 29, wherein step d) is carried out at a temperature the range of ≥0° C. to ≤40° C.
31. The process according to any of embodiments 1 to 30, wherein step a), b) and c) are carried out in a one-pot reaction.

EXAMPLES

The presently claimed invention is illustrated in detail by non-restrictive working examples which follow.

Methods

The characterization was by coupled High Performance Liquid Chromatography/mass spec-trometry (HPLC/MS), Gas chromatography (GC), by NMR or by melting points.

HPLC method: Agilent Eclipse Plus C18, 150 mm×4.6 mm ID×5 um

Gradient A=0.1% TFA in water, B=0.1% TFA in acetonitrile.

Flow=1.4 mL/min, column oven temperature=30° C.
Gradient program=10% B-100% B-5 min, hold for 2 min, 3 min-10% B.
Run Time=10 min
LCMS method 1: C18 Column (50 mm×3.0 mmx 3μ)
Gradient A=10 Mm ammonium formate in water, B=0.1% formic acid in acetonitrile
Flow=1.2 mL/min, column oven temperature=40° C.
Gradient program=10% B to 100% B in 1.5 min, hold for 1 min 100% B, 1 min-10% B
Run time: 3.75 min $^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplet, q=quartet, t=triplet, d=doublet and s=singlet.

Abbreviations used are: h for hour(s), min for minute(s), rt for retention time and ambient temperature for 20-25° C.

Example 1

Preparation of (1,3 E/Z)-1,3-bis(dimethylaminomethylene)thiourea

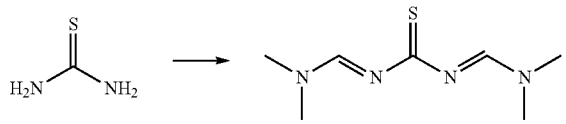

In a 16 L reactor thiourea (500 g), monochlorobenzene (MCB) (5 L) and dimethylformamide dimethyl acetal (2.19 L) were charged under nitrogen atmosphere. The reaction mass was stirred at 55 to 60° C. for 3 h. After 3 h, 2.5 L solvent (methanol and MCB) was distilled under vacuum to obtain (1,3E/Z)-1,3-bis(dimethylaminomethylene)thiourea as a suspension in MCB. The suspension was used as such in step b. [99% of theoretical yield, m/z=187 amu (M+H$^+$)], HPLC RT: 4.70
$^1$H NMR (300 MHz, CDCl$_3$): 3.17 (s, 6H), 3.20 (s, 6H), 8.92 (s, 2H).

Step a: Preparation of N'-(5-acetylthiazol-2-yl)-N,N-dimethyl-formamidine

To a suspension of (1,3E/Z)-1,3-bis(dimethylaminomethylene)thiourea in MCB was charged MCB (2 L) in a 16 L reactor. The jacket of the reactor was set to 45° C. and a solution of chloroacetone (0.65 L) in MCB (0.5 litre) was dosed over a period of 20 min under nitrogen atmosphere (Exotherm of 25-30° C. was observed during the addition of chloroacetone). After complete addition of chloroacetone, the reaction mass was allowed to come to 55-60° C. and stirred for 0.5 h. >99% conversion to N'-(5-acetylthiazol-2-yl)-N,N-dimethyl-formamidine was observed by HPLC. The reaction mass was as such subjected to the next step in the same reactor. [99% of theoretical yield, m/z=198 amu (M+H$^+$)]. HPLC RT: 6.05, $^1$H NMR (300 MHz, CDCl$_3$): 2.28 (s, 3H), 3.10 (s, 3H), 3.12 (s, 3H), 7.93 (s, 1H), 8.28 (s, 1H).

Step b: Preparation of 1-(2-aminothiazol-5-yl)ethanone

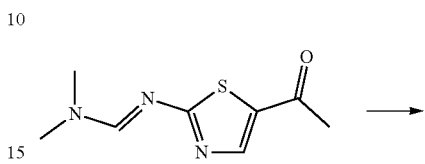

To the above reaction mass aq. HCl (35%, 2.5 L) was charged within 25 min at 55-60° C. (exotherm of 5° C. was observed). Demineralized water (0.5 L) was charged at 55-60° C. and stirred for 2 h. After 2 h, HPLC showed >99% conversion to the desired product. The stirrer was stopped and the aq. phase 1 was separated at 55-60° C. Aq. HCl (35%,1 L) was charged to the organic phase and the biphasic mixture was stirred for 15-20 min at the same temperature.

Again, the aqueous phase 2 was separated and combined with aq. phase 1. The combined aq. phases were used as such for the next step in the same reactor. [99% of theoretical yield, m/z=143 amu (M+H$^+$)]. HPLC RT: 4.49, $^1$H NMR (300 MHz, DMSOd$^6$): 2.34 (s, 3H), 7.91 (s, 1H), 7.99 (brs, 2H).

Step c: Preparation of 1-(2-chlorothiazol-5-yl)ethanone

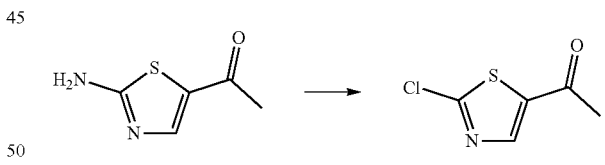

To the aqueous solution of step b, aq. HCl (35%, 1 L) was charged and the solution was cooled down to −7° C. CuSO$_4$·H$_2$O (0.16 kg) and NaCl (0.35 kg) were charged. A solution of NaNO$_2$ (0.94 kg) in water (1.2 L) was charged over a period of 2.5 h between −7 to 3° C. After complete addition, the reaction was stirred at 10 to 15° C. for 0.5 h. MCB (2 L) and water (2 L) were charged and stirred for 10 min. The aqueous phase was separated and extracted with MCB (1 L). The combined organic phases were washed with sat. aq. NaHCO$_3$ (1 L) and water (1 L). The organic phase was separated and MCB was distilled under vacuum to afford 1-(2-chlorothiazol-5-yl) ethanone (1.02 kg). [85% of theoretical yield over 4 steps. GCMS, m/z=161 amu.] HPLC RT: 6.94, $^1$H NMR (300 MHz, CDC$_3$): 2.58 (s, 3H), 8.08 (s, 1H).

Step d: Preparation of 2-chloro-1-(2-chlorothiazol-5-yl)ethanone

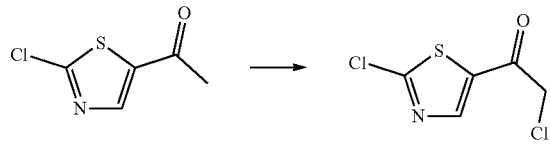

A 2L 3-necked flask equipped with a teflon-blade stirrer, an addition funnel and a thermo-pocket was charged with 1-(2-chlorothiazol-5-yl)ethanone (150 g) and acetonitrile (330 mL) under nitrogen atmosphere and cooled to 15 to 20° C. Sulfuryl chloride (73 mL was charged dropwise at 15 to 20° C. in 0.5 h. The reaction mass was warmed to ambient temperature and stirred for 5 h. The weak HCl salt of 2-chloro-1-(2-chlorothiazol-5-yl)ethanone precipitated out of the reaction; the suspension was cooled to 0 to 5° C. and stirred for 10 min. The precipitate was washed with cold acetonitrile (25 mL). The solid was dried under vacuum at 35° C. The weak HCl salt breaks down during drying to give 2-chloro-1-(2-chlorothiazol-5-yl)ethanone as beige colored solid. [80% of theoretical yield, m/z=195 amu (M+H$^+$)]. HPLC RT: 7.90. $^1$H NMR (300 MHz, CDC$_3$): 4.52 (s, 2H), 8.21 (s, 1H).

Example 2

Preparation of (1,3 E/Z)-1,3-bis(dimethylaminomethylene)thiourea

In a 1.6 L reactor thiourea (70 g), monochlorobenzene (MCB) (955 ml) and dimethylformamide dimethyl acetal (294 ml) were charged under nitrogen atmosphere. The reaction mass was stirred at 55 to 60° C. for 3 h. After 3 h, 385 ml solvent (methanol and MCB) was distilled under vacuum to obtain (1,3E/Z)-1,3-bis(dimethylaminomethylene)thiourea as a suspension in MCB.

The suspension was used as such in step b. [99% of theoretical yield, m/z=187 amu (M+H$^+$)], HPLC RT: 4.70

$^1$H NMR (300 MHz, CDCl$_3$): 3.17 (s, 6H), 3.20 (s, 6H), 8.92 (s, 2H).

Step a: Preparation of N'-(5-Acetylthiazol-2-yl)-N,N-Dimethyl-Formamidine

The suspension of (1,3E/Z)-1,3-bis(dimethylaminomethylene)thiourea in MCB was charged in a 1.6 L reactor. The jacket of the reactor was set to 55° C., vacuum 200 to 250 mbar was applied and a solution of chloroacetone (86.8 ml) in MCB (70 ml) was dosed over a period of 2 to 3 h using dip tube (Exotherm of 3-5° C. was observed during the addition of chloroacetone). After complete addition of chloroacetone, the reaction mass was stirred at 60° C. for 0.5 h. >99% conversion to N'-(5-acetylthiazol-2-yl)-N,N-dimethyl-formamidine was observed by HPLC. The reaction mass was as such subjected to the next step in the same reactor. [97% of theoretical yield, m/z=198 amu (M+H$^+$)]. HPLC RT: 6.05, $^1$H NMR (300 MHz, CDCl$_3$): 2.28 (s, 3H), 3.10 (s, 3H), 3.12 (s, 3H), 7.93 (s, 1H), 8.28 (s, 1H).

Step b: Preparation of 1-(2-Aminothiazol-5-yl)Ethanone

To the above reaction mass aq. HCl (35%, 407 ml) was charged within 40 min at 55 to 60° C. (exotherm of 5° C. was observed). Demineralized water (70 ml) was charged at 55-60° C. and stirred for 2 h. After 2 h, HPLC showed >99% conversion to the desired product. The stirrer was stopped and the aq. phase 1 was separated at 55-60° C. Aq. HCl (35%,166 ml) was charged to the organic phase and the biphasic mixture was stirred for 15-20 min at the same temperature. Again, the aqueous phase 2 was separated and combined with aq. phase 1. The combined aq. phases were used as such for the next step in the same reactor. [98% of theoretical yield, m/z=143 amu (M+H$^+$)]. HPLC RT: 4.49, $^1$H NMR (300 MHz, DMSOd$^6$): 2.34 (s, 3H), 7.91 (s, 1H), 7.99 (brs, 2H).

Step d: Preparation of 2-Chloro-1-(2-Chlorothiazol-5-yl) Ethanone

Method-1:

A 1L jacketed reactor equipped with a glass-blade stirrer and a thermo-pocket was charged with 55.5 wt. % solution of 1-(2-chlorothiazol-5-yl)ethanone in monochlorobenzene (180 g), rinse the flask with monochlorobenzene (72 ml) and acetonitrile (300 mL) under nitrogen atmosphere and cooled to 15 to 20° C. Chlorine gas (90 gm) was purged at 15 to 20° C. in 2-3 h. The reaction mass was stirred at 15 to 20° C. for 3 h. The weak HCl salt of 2-chloro-1-(2-chlorothiazol-5-yl) ethanone precipitated out of the reaction. Monochlorobenzene (200 ml) was added and the suspension was refluxed for 40 min. Solvent (MCB: ACN, 226 ml) was distilled out. To the residue water (102 ml was added) followed by 5% NaHCO$_3$ (90 ml). The organic phase was separated and again washed with water (100 ml). The organic phase was evaporated under vacuum give 2-chloro-1-(2-chlorothiazol-5-yl)ethanone as 24% MCB solution. [74% of theoretical yield, m/z=195 amu (M+H$^+$)]. HPLC RT: 7.90. $^1$H NMR (300 MHz, CDCl$_3$): 4.52 (s, 2H), 8.21 (s, 1H).

Method-2:

A 1L jacketed reactor equipped with a glass-blade stirrer and a thermo-pocket was charged with 1-(2-chlorothiazol-5-yl)ethanone (92 g), toluene (92 g) and acetonitrile (368 g). under nitrogen atmosphere at room temperature. Chlorine gas (45 gm) was purged at 25 to 30° C. in 2-3 h. The reaction mass was stirred at room temperature for 3 h. The reaction mass was cooled to 0 to 5° C. and stirred for 30 minutes. The solid 2-chloro-1-(2-chlorothiazol-5-yl)ethanone precipitated out of the solution was filtered and dried under vacuum. [73% of theoretical yield, m/z=195 amu (M+H$^+$)]. HPLC RT: 7.90. $^1$H NMR (300 MHz, CDCl$_3$): 4.52 (s, 2H), 8.21 (s, 1H).

Crystallization of 2-chloro-1-(2-chlorothiazol-5-yl)ethanone:

Crude material (571 g, 84.52%) was dissolved in IPA (856 ml) and heated at 60° C. to obtain a clear solution and stirred for 30 min and gradually cooled to 0° C. and stirred for 30 min. The solid was filtered and suck dried under vacuum to obtain 2-chloro-1-(2-chlorothiazol-5-yl)ethanone (443 g, 98.9 wt. %, 92% of theoretical yield) as beige colored solid.

It was found out that the addition rate of chloroacetone to 1,3-bis(dimethylaminomethylene)thiourea is critical. On the one hand, if chloroacetone is added too fast, the reaction cannot be controlled anymore and exceeds a temperature of 70° C. On the other hand, if chloroacetone is added too slowly, the yield of 1,3-bis(dimethylaminomethylene)thiourea decreases and other side products are formed that nega-tively impact the overall yield of the synthesis of 2-chloro-1-(2-chlorothiazol-5-yl)ethanone.

The following table 1 gives an overview of different addition rates. All examples were carried out in accordance with example 1a. However, in each case, the addition rate of chloroacetone was modified. Unknown impurities and a reverse impurity N,N-dimethyl-N'-(4-methylthiazol-2-yl) formamidine were detected.

TABLE 1

| Example | Addition rate chloroacetone [vol.-%] | Exotherm [° C.] | N'-(5-acetylthiazol-2-yl)-N,N-dimethyl-formamidine Yield [%] | reverse impurity [%] | Unknown impurity [%] |
|---|---|---|---|---|---|
| 1a | 5.0 | 44 to 68 | 99.0 | not detected | —not detected |
| 2a* | 10.0 | 44 to 85 | 97.0 | 1.5 | 1.4 |
| 3a | 2.5 | 45 to 67 | 97.0 | 3.0 | Not detected |
| 4a* | 1.6 | 45 to 66 | 94.0 | 5.0 | Not detected |
| 5a* | 1.1 | 45 to 65 | 93.5 | 6.4 | Not detected |
| 6a* | 0.8 | 45 to 50 | 95.3 | 2.8 | 0.8 |
| 7a* | 0.5 | 45 to 50 | 96.2 | 2.3 | 0.7 |

*not within the scope of the presently claimed invention

The invention claimed is:

1. A process for the preparation of 2-chloro-1-(2-chlorothiazol-5-yl)ethanone comprising:
   a) cyclization of 1,3-bis(dimethylaminomethylene)thiourea and chloroacetone to form N'-(5-acetylthiazol-2-yl)-N,N-dimethyl-formamidine,
   b) subjecting (5-acetylthiazol-2-yl)-N,N-dimethyl-formamidine to at least one acid to form 1-(2-aminothiazol-5-yl)ethanone,
   c) Sandmeyer reaction of 1-(2-aminothiazol-5-yl)ethanone to form 1-(2-chlorothiazol-5-yl)ethanone, and
   d) chlorination of 1-(2-chlorothiazol-5-yl)ethanone to form 2-chloro-1-(2-chlorothiazol-5-yl)ethanone,
wherein in step a) chloroacetone is added at a rate in a range of ≥2.0 vol.-%/minute to ≤8.0 vol.-%/minute, based on the total volume of chloroacetone.

2. The process according to claim 1, wherein in step a) chloroacetone is added at a rate in the range of ≥2.0 vol.-%/minute to ≤7.0 vol.-%/minute, based on the total volume of chloroacetone.

3. The process according to claim 1, wherein step a) is carried out at a temperature the range of ≥40° C. to ≤75° C.

4. The process according to claim 1, wherein in step a) a molar ratio of chloroacetone to 1,3-bis(dimethylaminomethylene)thiourea is in the range of ≥1.20:1.00 to ≤1.01:1.00.

5. The process according to claim 1, wherein step a) is carried out in the absence of any amine.

6. The process according to claim 1, wherein in step b) the at least one acid is selected from inorganic acids and organic acids.

7. The process according to claim 1, wherein step b) is carried out at a temperature the range of ≥20° C. to ≤110° C.

8. The process according to claim 1, wherein step c) is carried out in the presence of at least one nitrosating agent and at least one chlorine source.

9. The process according to claim 1, wherein step c) is carried out in the presence of at least one catalyst.

10. The process according to claim 1, wherein step c) is carried out at a temperature in the range of ≥−10° C. to ≤40° C.

11. The process according to claim 1, wherein step d) is carried out in the presence of at least one chlorinating agent.

12. The process according to claim 1, wherein step d) is carried out at a temperature the range of ≥0° C. to ≤40° C.

13. The process according to claim 1, wherein steps a), b) and c) are carried out in a one-pot reaction.

* * * * *